United States Patent [19]
Lunt et al.

[11] Patent Number: 5,260,291
[45] Date of Patent: Nov. 9, 1993

[54] TETRAZINE DERIVATIVES

[75] Inventors: Edward Lunt, Norfolk; Malcolm F. G. Stevens, Birmingham, both of England; Robert Stone, Montrose, Australia; Kenneth R. H. Wooldridge, Lincolnshire; Edward S. Newlands, London, both of England

[73] Assignee: Cancer Research Campaign Technology Limited, London, England

[21] Appl. No.: 781,020

[22] Filed: Oct. 18, 1991

Related U.S. Application Data

[63] Continuation-in-part of Ser. No. 607,221, Nov. 1, 1990, abandoned, which is a continuation of Ser. No. 456,614, Dec. 29, 1989, abandoned, which is a continuation of Ser. No. 338,515, Mar. 3, 1989, abandoned, which is a continuation of Ser. No. 135,473, Dec. 21, 1987, abandoned, which is a continuation of Ser. No. 40,716, Apr. 20, 1987, abandoned, which is a continuation of Ser. No. 885,397, Jul. 18, 1986, abandoned, which is a continuation of Ser. No. 798,365, Nov. 18, 1985, abandoned, which is a continuation of Ser. No. 712,462, Mar. 15, 1985, abandoned, which is a continuation of Ser. No. 586,635, Mar. 6, 1984, abandoned, which is a continuation of Ser. No. 410,656, Aug. 23, 1982, abandoned.

[30] Foreign Application Priority Data

Aug. 24, 1981 [GB] United Kingdom ............... 8125791

[51] Int. Cl.$^5$ ................. A61K 31/415; C07P 487/04
[52] U.S. Cl. ................................ 514/183; 544/179
[58] Field of Search ..................... 544/179; 514/183

[56] References Cited

FOREIGN PATENT DOCUMENTS

| | | |
|---|---|---|
| 571430 | 8/1988 | Australia . |
| 380256 | 5/1986 | Austria . |
| 1001617 | 12/1984 | Bangladesh . |
| 894175 | 2/1983 | Belgium . |
| 1197247 | 11/1985 | Canada . |
| 2932305 | 2/1981 | Fed. Rep. of Germany . |
| 734343 | 10/1981 | Finland . |
| 8214461 | 1/1985 | France . |
| 76863 | 9/1984 | Greece . |
| 186107 | 8/1984 | Hungary . |
| 53408 | 2/1989 | Ireland . |
| 66606 | 8/1987 | Israel . |
| 1152505 | 1/1987 | Italy . |
| 28587 | 7/1989 | Rep. of Korea . |
| 84347 | 6/1983 | Luxembourg . |
| 201668 | 5/1986 | New Zealand . |
| RP5512 | 8/1983 | Nigeria . |
| 128469 | 12/1984 | Pakistan . |
| 82/6120 | 8/1982 | South Africa . |
| 515176 | 7/1983 | Spain . |
| 8204817.4 | 6/1987 | Sweden . |
| 655114 | 3/1986 | Switzerland . |
| 18691 | 8/1983 | Taiwan . |
| 1447284 | 12/1988 | U.S.S.R. . |
| 2104522 | 6/1985 | United Kingdom . |

OTHER PUBLICATIONS

Lunt et. al., J. Med. Chem. vol. 30, pp. 357–366 (1987).

Primary Examiner—Bernard Dentz
Attorney, Agent, or Firm—Klauber & Jackson

[57] ABSTRACT

[3H]-Imidazo[5,1-d]-1,2,3,5-tetrazin-4-one derivatives of the formula:

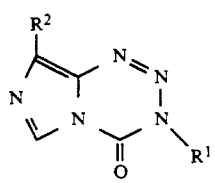

wherein $R^1$ represents hydrogen, or an alkyl, alkenyl or alkynyl group containing up to 6 carbon atoms, each such group being unsubstituted or substituted by from one to three substitutents selected from halogen atoms, alkoxy, alkylthio, alkylsulphinyl and alkylsulphonyl groups containing up to 4 carbon atoms, and optionally substituted phenyl groups, or $R^1$ represents a cycloalkyl group containing from 3 to 8 carbon atoms, and $R^2$ represents a carbamoyl group optionally N-substituted by one or two groups selected from alkyl and alkenyl groups containing up to 4 carbon atoms, and cycloalkyl groups containing 3 to 8 carbon atoms, are new therapeutically useful compounds possessing antineoplastic and immunomodulatory activity.

33 Claims, No Drawings

TETRAZINE DERIVATIVES

This application is a continuation-in-part of co-pending application Ser. No. 07/607,221, filed on Nov. 1, 1990, now abandoned, which is a continuation of Ser. No. 07/456,614, filed on Dec. 29, 1989, now abandoned; which is a continuation of application Ser. No. 07/338,515 filed on Mar. 3, 1989, abandoned; which is a continuation of applicaton Ser. No. 07/135,473, filed on Dec. 21, 1987, abandoned; which is a continuation of application Ser. No. 07/040,716, filed on Apr. 20, 1987, abandoned; which is a continuation of application Ser. No. 06/885,397, filed on Jul. 18, 1986, abandoned; which is a continuation of application Ser. No. 06/798,365 filed on Nov. 18, 1985, abandoned; which is a continuation of application Ser. No. 06/712,462 filed on Mar. 15, 1985, abandoned; which is a continuation of Ser. No. 06/586,636, filed on Mar. 6, 1984, abandoned; which is a continuation of application Ser. No. 06/410,656 filed on Aug. 23, 1982, abandoned.

This invention relates to new [3H -imidazo-5,1-d]-1,2,3,5-tetrazin-4-one derivatives, to processes for their preparation and to pharmaceutical compositions containing them.

The compounds of the present invention are the [3H]-imidazo[5,1-d]-1,2,3,5-tetrazin-4-one derivatives of the general formula:

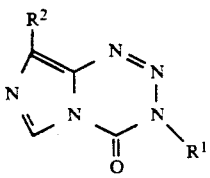

wherein $R^1$ represents a hydrogen atom, or a straight- or branched-chain alkyl, alkenyl or alkynyl group containing up to 6 carbon atoms, each such group being unsubstituted or substituted by from one to three substituents selected from halogen (i.e. bromine, iodine or, preferably,cblorine or fluorine) atoms, straight- or branched-chain alkoxy, (e.g. methoxy), alkylthio, alkylsullihinyl and alkylsulphonyl groups containing up to 4 carbon atoms, and optionally substituted phenyl groups, or $R^1$ represents a cycloalkyl group, and $R^2$ represents a carbamoyl group which may carry on the nitrogen atom one or two groups selected from straight- and branched-chain alkyl and alkenyl groups,each containing up to 4 carbon atoms, and cycloalkyl groups, e.g. a methylcarbamoyl cr dimethylcarbamoyl group.

When the symbol $R^1$ represents an alkyl, alkenyl or alkynyl group substituted by two or three halogen atoms, the aforesaid halogen atoms may be the same or different. When the symbol $R^1$ represents an alkyl, alkenyl or alkynyl group substituted by one, two or three optionally substituted phenyl groups the optional substituents on the phenyl radical(s) may be selected from, for example, alkoxy and alkyl groups containing up to 4 carbon atoms (e.g. methoxy and/or methyl group(s)) and the nitro group; the symbol $R^1$ may represent, for exainle, a benzyl or p-methoxybenzyl group. Cycloalkyl groups within the definitions of symbols $R^1$ and $R^2$ contain 3 to 8, preferably 6, carbon atoms.

Preferred tetrazine derivatives of general formula I are those wherein $R^1$ represents a straight-or branched-chain alkyl group containing from 1 to 6 carbon atoms optionally substituted by one or two halogen (preferably chlorine, fluorine or bromine) atoms or by an alkoxy group containing 1 to 4 carbon atoms (preferably methoxy) or by a phenyl group (optionally substituted by one or two alkoxy groups containing from 1 to 4 carbon atoms, preferably methoxy), or $R^1$ represents an alkenyl group containing 2 to 6 carbon atoms (preferably allyl) or a cyclohexyl group.

More particularly preferred tetrazine derivatives are those of general formula I wherein $R^1$ represents a straight- or branched-chain alkyl group containing from 1 to 6 carbon atoms, and more especially from 1 to 3 carbon atoms, unsubstituted or substituted by a halogen, preferably chlorine or fluorine, atom. More especially $R^1$ represents a methyl or 2-haloalkyl, e.g. 2-fluoroethyl or, preferably,2-chloroethyl, group.

Preferably $R^2$ represents a carbamoyl group or a monoalkylcarbamoyl, e.g. methylcarbamoyl, or monoalkenylcarbamoyl group.

The present invention also includes salts of the compounds of general formula I wherein $R^1$ represents a hydrogen atom and $R^2$ is as hereinbefore defined, more especially alkali metal, e.g. sodium, salts, and whenever the context so permits reference to the compounds of general formula I in this specification is meant to include reference to the said salts. The salts are particularly useful as interemdiates.

According to a feature of the present invention, the compounds of general formula I, wherein $R^2$ is as hereinbefore defined and $R^1$ is other than hydrogen, are prepared by the reaction of a compound of the general formula:

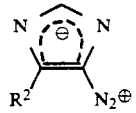

(wherein $R^2$ is as hereinbefore defined) with an isocyanate of the general formula:

$$R^3NCO \qquad III$$

wherein $R^3$ represents an alkyl, alkenyl or alkynyl group, optionally substituted by one to three substituents selected from halogen atoms, alkoxy, alkylthio, alkylsulphinyl and alkylsulphonyl groups and optionally substituted phenyl groups, or represents a cycloalkyl group, within the definition of $R^1$ hereinbefore recited. The reaction may be effected in the absence or presence of an anhydrous organic solvent, for example a chlorinated alkane, e.g. dichloromethane, or ethyl acetate, acetonitrile, N.-methylpyrrolid-2-one or, preferably, hexamethylphosphoramide, at a temperature between 0° and 70° C., e.g. at the ambient temperature. The reaction may be continued for up to 30 days. Light should preferably be excluded from the reaction mixture.

According to a further feature of the present invention, the compounds of general formula I, wherein $R^2$ is as hereinbefore defined and $R^1$ is other than hydrogen, are prepared by the reaction of a compound (within general formula I) of the general formula:

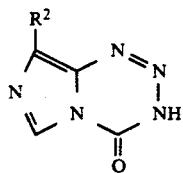

IV (wherein $R^2$ is as hereinbefore defined) or an alkali metal, e.g. sodium, salt thereof with a compound of the general formula:

$$R^3X \qquad V$$

wherein $R^3$ is as hereinbefore defined, and X represents the acid residue of a reactive ester, for example a halogen (e.g. chlorine) atom, or a sulphuric or sulphonic ester residue, e.g. a methoxysulphonyloxy, methanesulphonyloxy, or toluene-a-sulphonyloxy group. When $R^3$ in a compound of general formula V represents a haloalkyl, haloalkenyl or haloalkynyl group, the acid residue of a reactive ester represented by X will be selected from those known to be not less reactive than the halogen atom substituent in $R^3$. When X in a compound of general formula V represents a halogen atom, an alkali metal salt of the compound of general formula IV is preferably used and when X in a compound of general formula V represents a halogen atom and $R^3$ is a haloalkyl, haloalkenyl or haloalkynyl group wherein the halogen atom is the same as that represented by X, an excess of the dihalo compound of general formula V is preferably used. The reaction of a compound of general formula IV or alkali metal salt thereof with a compound of general formula V, wherein $R^3$ and X are as hereinbefore defined, may be carried out in a suitable anhydrous inert organic solvent, for example dichloromethane, acetonitrile or N-methylpyrrolid-2-one or mixtures thereof, at a temperature of from 0° C. to 120° C. and, when a compound of general formula IV is used, in the presence of an acid-binding agent, for example an alkali metal, e.g. sodium or potassium, carbonate or bicarbonate.

As a further feature of the invention, compounds of general formula IV (i.e. compounds of general formula I wherein $R^1$ represents a hydrogen atom and $R^2$ is as hereinbefore defined) or alkali metal salts thereof are prepared by the reaction of a compound of general formula II with a compound of the general formula:

$$R^4NCO \qquad VI$$

wherein $R^4$ represents an alkali metal (e.g. sodium) atom or a protecting group such as a benzyl or p-methoxybenzyl group, followed, when $R^4$ represents a protecting group, by the replacement of the protecting group by a hydrogen atom in the compound thus obtained of the general formula:

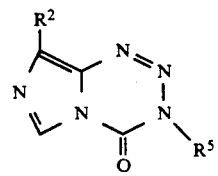

VII wherein $R^2$ is as hereinbefore defined, and $R^5$ represents a protecting group such as a benzyl or p-methoxybenzyl group, by methods known per se. Reaction of a compound of general formula II with a compound of general formula VI wherein $R^4$ represents a protecting group may be effected as hereinbefore described for the reaction of a compound of general formula II with a compound of general formula III. Reaction of a compound of general formula II with a compound of general formula VI, wherein $R^4$ represents an alkali metal atom, may be effected in a suitable inert organic solvent, e.g. ethanol, acetonitrile or N-methylpyrrolidone, optionally in the presence of an acid, at a temperature of from 0° to 120° C. The group $R^5$ of compounds of general formula VII, wherein $R^5$ is as hereinbefore defined, may be replaced by a hydrogen atom by methods known per se to give a compound of general formula IV.

Compounds of general formula II may be prepared by the application or adaptation of methods known per se. for example methods described by Shealy Y.F., Struck R.F., Holum L.B. and Montgomery J.A., J. Org. Chem. (1961), 26, 2396.

Compounds of general formulae III, V and VI may be prepared by the application or adaptation of methods known per se.

By the term 'methods known per se' as used in the present specification is meant methods heretofore used or described in the literature.

The new tetrazine derivatives of general formula I possess valuable antineoplastic activity, for example against carcinomas, melanomas, sarcomas, lymphomas and leukaemias. They possess useful activity against glioma and mycosis fungoides. They have proved particularly active in mice at daily doses between 0.5 and 16 mg/kg animal body weight, administered intraperitoneally, against TLX5 (S) lymphomas according to the procedure of Gescher et al, Biochem. Pharmacol. (1981), 30, 89, and ADJ/PC6A and M5076 (reticulum cell sarcoma). Against leukaemia L1210, grafted intraperitoneally, intracerebrally and intravenously, and P388, according to the procedure described in "Methods of Development of New Anticancer Drugs" (NCI Monograph 45, March 1977, pages 147–149, National Cancer Institute, Bethesda, United States), the compounds were active both intraperitoneally and orally at doses of between 2.5 and 10 mg/kg animal body weight. Inhibition of both primary tumour and metastasis was obtained against the Lewis lung carcinoma by similar dosage regimes. Against the B16 melanoma and C38 tumour in mice (NCI Monograph 45, op cit.) the compounds were active intraperitoneally at doses of between 6.25 and 25 mg/kg animal body weight.

The tetrazine derivatives also possess valuable immunomodulatory activity and are of use in the treatment of organ grafts and skin grafts and in the treatment of immunological diseases.

Important individual compounds of general formula I include the following:

8-carbamoyl-3-methyl-[3H]-imidazo[5,1-d]-1,2,3,5-tetrazin-4-one    A, 8-carbamoyl-3-n-propyl-[3H]-imidazo[5,1-d]-1,2,3,5-tetrazin-4-one    B, 8-carbamoyl-3-(2-chloroethyl)-[3H]-imidazo-[5,1-d]-1,2,3,5-tetrazin-4-one    C, 3-(2-chloroethyl)-8-methylcarbamoyl-[3H]-imidazo[5,1-d]-1,2,3,5-tetrazin-4-one    D, 8-carbamoyl-3-(3-chloropropyl)-[3H]-imidazo-[5,1-d]-1,2,3,5-tetrazin-4-one    E, 8-carbamoyl-3-(2,3-dichloropropyl)-[3H]-imidazo[5,1-d]-1,2,3,5-tetrazin-4-one  F,
3-allyl-8-carbamoyl-[3H]-imidazo[5,1-d]-1,2,3,5-tetrazin-4-one  G,
3-(2-chloroethyl)-8-dimethylcarbamoyl-[3H]-imidazo[5,1-dl-1,2,3,5-tetrazin-4-one  H,
3-(2-bromoethyl)-8-carbamoyl-[3H]-imidazo-5,1-d]-1,2,3,5-tetrazin-4-one  I,
3-benzyl-8-carbamoyl-[3H]-imidazo[5,1-d]-1,2,3,5-tetrazin-4-one  J,
8-carbamoyl-3-(2-methoxyethyl)-[3H]-imidazo[5,1-d]-1,2,3,5-tetrazin-4-one  K,
8-carbamoyl-3-cyclohexyl-[3H]-imidazo[5,1-d]-1,2,3,5-tetrazin-4-one  L,
and 8-carbamoyl-3-(Wmethoxybenzyl)-[3H]imidazo[5,1-d]-1,2,3,5-tetrazin-4-one.  M Compounds A and D, and especially C, are of particular importance.

The letters A to M are allocated to the compounds for easy reference later in the specification.

The following Examples illustrate the preparation of compounds of general formula I according to the present inventions and the Reference Example thereafter illustrates the preparation of intermediates.

EXAMPLE 1

Compound A

4[5]-Diazoimidazole-5[4]-carboxamide (500 mg) was suspended in methyl isocyanate (3.0 ml) and stirred in the dark, at ambient temperature, for 21 days. The reaction mixture was then diluted with anhydrous diethyl ether and filtered. The residue was washed quickly with anhydrous methanols then with anhydrous diethyl ether, and dried in air, in the dark, at ambient temperature, to give 8-carbamoyl-3-methyl-[3H]-imidazo[5,1-d]-1,2,3,5-tetrazin-4-one, in the form of a light brown microcrystalline solid (198 mg), m.p. 210° C. (with effervescence and darkening from 160° to 210° C.). [Elemental analysis:- found: C,36.8; H,3.10; 44.2%; $C_6H_6N_6O_2$ requires: C,37.1; H,3.09; N,43.3%].

EXAMPLE 2

Compound B

4[5]-Diazoimidazole-5[4]-carboxamide (300 mg) was suspended in anhydrous dichloromethane (10 ml) and treated with an excess of n-propyl isocyanate. The reaction mixture was then stirred in the dark, at ambient temperatures for 30 days. The reaction mixture was then filtered and the residue was washed quickly with anhydrous diethyl ether#and dried in air, in the dark, at ambient temperatures to give 8-carbamoyl-3-n-propyl-[3H]-imidazo[5,1-d]-1,2,3,5-tetrazin-4-one (102 mg), in the form of a pale pink powder,, m.p. 167° C. (with effervescence).

[Elemental analysis:- found: C,43.4; H#4.57; N,38.0%;
$C_8H_{10}N_6O_2$ requires: C.43.2-, H4.53, N,3 7. 8%].

EXAMPLE 3

Compound C

4[5]-Diazoimidazole-5[4]-carboxamide (300 mg) was suspended in anhydrous dichloromethane (10 ml) and 2-chloroethyl isocyanate (1.0 ml) was added. The reaction mixture was then stirred in the dark, at ambient temperatures for 30 days. The cream-coloured suspension thus obtained was filtered and the residue was washed quickly with anhydrous diethyl ether and dried in air, in the dark, to give 8-carbamoyl-3-(2-chloroethyl)-[3H]-imidazo[5,1-d]-1,2,3,5-tetrazin-4-one (483 mg), in the form of a cream-coloured powder, m.p. 158° C. (with vigorous decomposition). [Elemental analysis:- found: C,34.7; H,3.01; N,34.9%; $C_7H_7ClN_6O_2$ requires: C,34.7; H,2.91; N,34.7%].

Repetition of the above procedure has also given 8-carbamoyl-3-(2-chloroethyl)-[3H]-imidazo[5,1-d]-1,2,3,5-tetrazin-4-one in another polymorphic form, m.p. 164°-165° C. (with decomposition).

EXAMPLE 4

Compound A

A suspension of 4[5]-diazoimidazole-5[4]-carboxamide (1.37 g) in ethyl acetate (20 ml) was treated with methyl isocyanate (7.0 g) and was stirred in a closed vessel in the dark at room temperature for 3 weeks. The resulting solid was filtered off and washed with diethyl ether to give 8-carbamoyl-3-methyl-[3H]-imidazo[5,1-d]-1,2,3,5-tetrazin-4-one (1.9 g) , in the form of a cream-coloured solid, m.p. 212° C. (with effervescence).

This material was recrystallised from three different solvent systems to give three different products, each of which had a slightly different IR spectrum. The three products were probably all polymorphs of 8-carbamoyl-3-methyl-[3H]-imidazo[5,1-d]-1,2,3,5-tetrazin-4-one.

(i) Colourless needles were obtained from a 3:1 v/v mixture of acetone and water, $\nu_{max}$ 3410, 3205 1758, 1730 and 1678 cm$^{-1}$, m.p. 210° C. (with effervescence).

(ii) White microcrystals were obtained from a 1:3 v/v mixture of acetone and water, $\nu_{max}$ 3430, 3200, 1740 and 1675 cm$^{-1}$, m.p. 210° C. (with effervescence).

(iii) A granular solid was obtained from hot water, $\mu_{max}$ 3450, 3380, 3200, 1742, 1688 and 1640 cm$^{-1}$, m.p. 215° C. (with effervescence) (darkening from 200° C.)

EXAMPLE 5

Compound B

A suspension of 4[5]-diazoimidazole-5[4]-carboxamide (1.37 g) in acetonitrile (20 ml) was treated with n-propyl isocyanate (6.5 g) and was stirred in a closed vessel in the dark at room temperature for 3 weeks. The resulting pink solid was filtered off, washed with diethyl ether, and recrystallised from a mixture of water and acetone (1:4 v/v), to give 8-carbamoyl-3-n-propyl-[3H]-imidazo[5,1-d]-1,2,3,5, tetrazin-4- one (1.6 g), m.p. 170°-172° C. (with effervescence). By concentration of the recrystallisation mother liquor there was obtained a furtherquantity (0.2 g) of the same product.

EXAMPLE 6

Compound C

A suspension of 4[5]-diazoimidazole-5[4]-carboxamide (1.0 g) in ethyl acetate (30 ml) was treated with 2-chloroethyl isocyanate (3.3 ml) and the mixture was stirred in the dark, at ambient temperature, for 6 days. The reaction mixture was then diluted with diethyl ether and the resulting solid was filtered off, to give 8-carbamoyl-3-(2-chloroethyl)-[3H]-imidazo[5,1-d]-1,2,3,5-tetrazin-4-one (1.6 g) in the form of a colourless solid, m.p. 164°-165° C. (with decomposition). [Elemental analysis:- found: C,34.5; H,2.88; N,34.5; Cl,14.6%; $C_7H_7ClN_6O_2$ requires C,34.65; H,2.91; N,34.65; Cl,14.61%].

EXAMPLE 7

Compound C

A suspension of 4[5]-diazoimidazole-5[4]carboxamide (5.0 g) in a mixture of dichloromethane (158 ml) and N methylpyrrolid-2-one (8.3 ml) was treated with 2-chloroethyl isocyanate (16.7 ml) and the mixture was stirred in the dark at ambient temperature for 14 days. The reaction mixture was then diluted with anhydrous diethyl ether and the resulting solid was filtered off and washed with diethyl ether, to give 8-carbamoyl-3-(2-chloroethyl)-[3H]-imidazo[5,1-d]-1,2,3,5-tetrazin-4-one (6.3 g), in the form of a purple-tinged solid, m.p. 164°–165° C. (with decomposition). [Elemental analysis:- found: C,34.7; H,2.95; N,34.5; Cl,14.4%; $C_7H_7ClN_6O_2$ requires: C,34.65; H,2.91; N,34.65; Cl,14.61%].

EXAMPLE 8

Compound C

A suspension of 4[5]-diazoimidazole-5[4]carboxamide (145 g) in ethyl acetate (2175 ml) was treated with 2-chloroethyl isocyanate (478.5 ml) and stirred at 30° C., with the exclusion of light, for 2 days. The mixture was then filtered to give 8-carbamoyl-3-(2-chloroethyl)-[3H]-imidazo[5,1]-1,2,3,5, tetrazin-4-one (250 g), in the form of a peach-coloured solid, m.p. 166° C.

EXAMPLE 9

Compound A

A stirred suspension of 4[5]-diazoimidazole-5[4]-carboxamide (2.2 g) in a mixture of dichloromethane (70 ml) and N-methylpyrrolid-2-one (3.5 ml) was treated with methyl isocyanate (7.0 ml) and stirred at ambient temperature for 4 weeks. The mixture was diluted with diethyl ether and the resulting solid was filtered off, to give 8-carbamoyl-3-methyl-[3H]-imidazo[5,1-d]-1,1,2,3,5-tetrazin-4- one (2.38 g), in the form of a pale purple solid, m.p. 202°–203° C. (with decomposition). [Elemental analysis:- found: C,36.8; H,2.94; N,43.1%; $C_6H_6N_6O_2$ requires: C.37.11; H,3.14; N,43.3%].

A polymorphic form of 8-carbamoyl-3-methyl[-3H]-imidazo[5,1-d]-1,2,3,5-tetrazin-4-one was obtained by dissolving it in acetonitrile, filtering, concentration of the filtrate to dryness, and trituration of the resulting residue with diethyl ether. This material was in the form of an orange-tinged solid, m.p. about 200° C. (with decomposition). [Elemental analysis: C,37.4; H,3.26; N,43.5%]. Its NMR spectrum in dimethylsulphoxide-$D_6$ was identical to that of the abovementioned pale purple solid, but its IR spectrum (KBr disc) showed some differences.

EXAMPLE 10

Compound D

A stirred solution of sodium nitrite (0.64 g) in water (4.6 ml) was cooled to 5°–10° C. and treated dropwise at that temperature with a solution of 5-amino-4-methylcarbamoylimidazole (1.00 g) in aqueous acetic acid (1M; 14.3 ml) during 5 minutes. Stirring was continued at 5°–10° C. for 5 minutes. The dark red solution was then extracted with ethyl acetate (4×35 ml) and the combined extracts were dried over magnesium sulphate. The resulting solution contained crude 4[5]-diazo-5[4]-methylcarbamoylimidazole, which was unstable and was used immediately for the next stage without further purification.

The solution of 4[5]-diazo-5[4]-methylcarbamoylimidazole in ethyl acetates prepared as described above, was treated with 2-chloroethyl isocyanate (4.3 ml) and was allowed to stand in the dark for 1 day. The solution was then evaporated at 40° C./10 mm Hg and the residue was triturated with petroleum ether (b.p. 40°–60° C.) to give an orange gum (4.23 g). This gum was treated with ethyl acetate (50 ml) and filtered, and the filtrate was evaporated at 40° C./10 Mm Hg to give an orange gum (2.94 g). This gum was purified by medium pressure column chromatography on silica gel, eluting with a mixture of ethyl acetate and acetonitrile (4:1 v/v), to give 3-(2-chloroethyl)-8-methylcarbamoyl-[3H]-imidazo[5,1-d]1,2,3,5-tetrazin-4-one (0.81 g), in the form of a purple solid, m.p. 120°–122° C. (with decompositon). [Elemental analysis:- found: C,37.3; H,3.58; N,31.9%; $C_8H_9ClN_6O_2$ requires: C,37.4; H,3.53; N,32.7%].

EXAMPLE 11

Compound E

A suspension of 4[5]-diazoimidazole-5[4]-carboxamide (1.0 g) in ethyl acetate (50 ml; dried over anhydrous potassium carbonate) was treated with 3-chloropropyl isocyanate (4.86 g) and the mixture was stirred at ambient temperature for 3 days. The reaction mixture was then diluted with anhydrous diethyl ether and the resulting solid was filtered off, and washed with anhydrous diethyl ethers to give 8-carbamoyl-3-(3-chloropropyl)-[3H]-imidazo[5,1-d]-1,2,3,5 -tetrazin-4-one (1.05 g) in the form of a pink solid, m.p. 153°–154° C. (with decomposition). ]Elemental analysis:- found: C,37.1; H,3.42; N,32.7; Cl,13.8%; $C_8H_9ClN_6O_2$ requires: C,37.4; H,3.53; N,32.8; Cl,13.8%].

EXAMPLE 12

Compound F

By proceeding in a manner similar to that described hereinbefore in Example 11 but replacing the 3-chloropropyl isocyanate used as a starting material by the appropriate quantity of 2,3-dichloropropyl isocyanates there was prepared 8-carbamoyl-3-(2,3-dichloropropyl)-[3H]imidazo[5,1-d]-1,2,3,5-tetrazin-4-one, in the form of an off-white solid, m.p. 153°–155° C. (with decomposition). [Elemental analysis:- found: C,32.7; H,2.51; N,28.7; Cl,24.1%; $C_8H_8Cl_2N_6O_2$ requires C,33.0; H,2.77; N,28.9; Cl,24.49/.].

EXAMPLE 13

Compound G

Stirred allyl isocyanate (4.5 ml, redistilled immediately before use) was treated with 4L5]-diazoimidazole-5[4]-carboxamide (1.0 g) and then with hexamethylphosphoramide (20 ml). The mixture was stirred at ambient temperature in the dark for 18 hours and then it was diluted with anhydrous diethyl ether and filtered. The resulting colourless solid was washed with anhydrous diethyl ether, to give 3-allyl-8-carbamoyl-E3H]-imidazo[5,1-d]-1,2,3,5-tetrazin-4-one (1.6 g),in the form of a colourless solid, m.p. 149°–150° C. [$\nu_{max}$(KBr disc): 1730, 1675 cm$^{-1}$; NMR in DMSO-d$_6$: singlets at 8.75, 7.67 and 7.60δ; double double triplet at 6.02 δ (J=5.5, 8, 10 Hz), double doublet at 5.35 δ (J=1.5, 8 Hz) and 5.20 δ (J=1.5, 10 Hz) and doublet at 4.88 δ (J=5.5)].

EXAMPLE 14

Compound H

A solution of 4[5]-diazo-5[4]-dimethylcarbamoylimidazole (1.59 g; prepared as described in Reference Example 1 hereafter) in dry ethyl acetate (57 ml) was treated with 2-chloroethyl isocyanate (6.36 g) and stirred at room temperature in the dark for 24 hours. The solution was then evaporated in vacuo at 35° C., finally at 0.1 Mm Hg to remove the excess of 2-chloroethyl isocyanate. The residual liquid was purified by medium pressure column chromatography on silica gel, eluting with a mixture of ethyl acetate and acetonitrile (4:1 v/v), to give 3-(2-chloroethyl)-8-dimethylcarbamoyl[3H]-imidazo[5,1-d]-1,2,3,5-tetrazin-4-one (0.82 g), in the form of colourless crystals#m.p. 114°-116° C. [Elemental analysis:- found: C.39.7; H,3.95; N,30.8%; $C_9H_{11}ClN_6O_2$ requires: C,39.9; H,4.10; N,31.0%].

EXAMPLE 15

Compound I

A stirred suspension of 4[5]-diazoimidazole-5[4]-carboxamide (1.0 g) in hexamethylphosphoramide (4 ml) was treated with 2-bromoethyl isocyanate (4.5 ml) and the mixture was stirred in the dark, at ambient temperature, for 2 days. The reaction mixture was then diluted with anhydrous diethyl ether and the resulting solid was filtered off, and washed with anhydrous diethyl ether, to give 3-(2-bromoethyl)-8-carbamoyl-[3H]-imidazo[5,1-d]-1,2,3,5-teirazin-4-one (1.17 g), in the form of a colourless solid, m.p. 156°-157° C. (with decomposition). [Elemental analysis:- found: C,29.5; N,2.36; N,29.1; Br,27.3%; $C_7H_7BrN_6O_2$ requires: C,29.3; H,2.46; N,29.3; Br,27.8%].

EXAMPLE 16

Compound J

By proceeding in a manner similar to that described hereinbefore in Example 15 but replacing the 2-bromoethyl isocyanate used as a starting material by the appropriate quantity of benzyl isocyanate, there was prepared 3-benzyl-B-carbamoyl-[3H]-imidazo[5,1-d]-1,2,3,5-tetrazin-4-one (0.83 g), in the form of a buff-coloured solid, m.p. 176°-177° C. (with decomposition). [Elemental analysis:- found: C,53.6; H,3.66; N,31.0%; $C_{12}H_{10}N_6O_2$ requires: C,53.3; H,3.73; N,31.1%].

EXAMPLE 17

Compound K

A suspension of 4[5]-diazoimidazole-5[4]carboxamide (0.3 g) in acetonitrile (5 ml) was treated with 2-methoxyethyl isocyanate (0.5 g) and the mixture was stirred at between 45° and 47° C. in the dark for 24 hours. The resulting solid was filtered off and washed with diethyl ether, to give crude 8-carbamoyl-3-(2-methoxyethyl)-[3H]-imidazo[5,1-d]-1,2,3,5-tetrazin-4-one (0.45 g), m.p. 145°-147° C. (with decomposition).

The product was purified by recrystallisation from aqueous acetone to give pink rosettes, or from aqueous dimethylsulphoxide to give colourless needles, m.p. 164°-165° C. (with decortposition). [Elemental analysis: C,40.4; H,4.20; N,35.2%; $C_8H_{10}N_6O_3$ requires: C,40.34; H,4.20; N,35.2%].

EXAMPLE 18

Compound L

A suspension of 4[5]-diazoimidazole-5[4]carboxamide (0.30 g) in acetonitrile (10 ml) was treated with cyclohexyl isocyanate (1.0 g) and the mixture was stirred at 60° C. in the dark for 3 days. The resulting solid was filtered off and washed with a mixture of ethanol and 0.880 aqueous ammonia (100:0.5 v/v; 20 ml) for one minute, to give 8-carbamoyl-3-cyclohexyl-[3H]-imidazoE5,1-d]-1,2,3,5 -tetrazin-4-one (0.015 g), m.p. 196° C. (with effervescence).

EXAMPLE 19

Compound J

A suspension of 4[5]-diazoimidazole-5[4]carboxamide (0.4 g) in acetonitrile (10 ml) was treated with benzyl isocyanate (0.6 g) and the mixture was stirred at 60° C. in the dark overnight. The reaction mixture was then cooled and filtered, to give 3-benzyl-8-carbamoyl-[3H]-imidazo[5,1-d]-1,2,3,5-tetrazin-4-one (0.75 g), in the form of a pale pink solid, m.p. 187°-188° C. (with effervescence).

EXAMPLE 20

Compound M

A suspension of 4[5]-diazoimidazole-5[4]carboxamide (0.1 g) and Wmethoxybenzyl isocyanate (0.4 g) in acetonitrile (5 ml) was stirred at 60° C. in the dark for 4 hours. The resulting pale pink solid was filtered off, and washed repeatedly with cold diethyl ether, to give B-carbamoyl-3-(p-methoxybenzyl)-[3H]-imidazo[5,1-d]-1,2,3,5-tetrazin-4-one (0.23 g), m.p. 180°-182° C. (with effervescence).

EXAMPLE 21

By proceeding in a similar manner to the foregoing Examples, there was prepared 8-(N-allyl-carbamoyl)-3-(2-chloroethyl)-[3H]-imidazo[5,1-d]- 1,2,3,5-tetrazin-4-one [I.R. 1750 cm$^{-1}$; NMR (in DMSO-d$_6$: multiplets 3.96, 5.06 and 5.84 ppm: triplets 4.60 and 6.2 ppm: singlet 8.78 ppm], from 5-amino-4-allylcarbamoylimidazole via 5-diazo-4-allylcarbamoylimidazole.

The 5-amino-4-allylcarbamoylimidazole was prepared from 5-nitro-4- allylcarbamoylimidazole (m.p. 218°-220C.) by reduction by means of titanous chloride.

REFERENCE EXAMPLE (i) An intimate mixture of 5-nitroimidazole-4-carboxylic acid (2.0 g) and phosphorus pentachloride (2.67 g) was stirred and heated in an oil bath at 120° C. for 1 hour. The resulting yellow slurry was evaporated at 60° C./0.1 nun Hg for 30 minutes, to give 1,6-dinitro-5H,10H-diimidazo[1,5-a:1',5'-d]pyrazine-5,10-dione (1.90 g) in the form of a yellow solid, m.p. 249°-251° C. (with decomposition). [$\nu_{max}$(KBr disc) 1750 cm$^{-1}$; m/e 278 (M+)].

Windaus, Ber., 1923, 56, 684 and Gireva, Chem. Abs. 59, 1622e, using the same method, describe their products as "5-nitroimidazole-4-carbonyl chloride".

(ii) Aqueous diffethylamine solution (25% w/v; 60 ml) was cooled to between 0° and 5° C. and treated portionwise, with stirring, with 1,6-dinitro-5H,10H-diimidazo[1,5-a:1', 5'-d]pyrazine-5,10-dione (6.0 g) in that temperature range. The resulting deep purple solution was stirred for 2 hours. The solution was evaporated at 50° C./10 mm Hg and then acidified by treatment with concentrated hydrochloric acid, to give an orange solution. This solution was extracted with ethyl acetate (7×200 ml), and the combined extracts were dried over magnesium sulphate, and evaporated, to give a yellow solid (6.6 g). This solid was triturated with toluene (50 ml) and then recrystallised from ethyl acetate, to give 5[4]-nitro-4[5]-dimethylcarbamoylimidazole (2.53 g), in the form of yellow crystals, m.p. 193°-195° C. [Elemental analysis:- found: C,38.9; H,4.23; N,30.4%; $C_6H_8N_4O_3$ requires: C, 39.1; H,4.38; N,30.4%].

(iii) A solution of 5[4]-nitro-4[5]-dimethylcarbamoylimidazole (1.62 g) in dry dimethylformamide (32 ml) was treated with platinum oxide (0.32 g) and shaken under hydrogen at atmospheric pressure and room temperature. After 3 hours, hydrogen absorption was complete (710 ml). The mixture was treated with charcoal and filtered through diatomaceous earth. The dark brown filtrate was evaporated at 50° C./0.1 rm Hg and the resulting residue was triturated with diethyl ether to give crude 5[4]-amino-4[5]-dimethylcarbamoylimidazole (1.75 g), in the form of a dark brown crystalline solid, m.p. 179°-181° C. [$\nu_{max}$(KBr disc) 1595 cm$^{-1}$; NMR in DMSO-d$_6$: singlets at 3.2 and 7.0$\delta$], which was still contaminated with colloidal platinum and which was used in the next stage without further purification.

(iv) A stirred solution of sodium nitrite (0.79 g) in water (5.7 ml) was cooled to between 5° and 10° C. and treated, dropwise, within this temperature range, with a solution of 5[4]-amino-4[5]-dimethylcarbamoylimidazole (1.75 g) in aqueous acetic acid (1M; 17.6 ml) during 5 minutes. The resulting solution was extracted with ethyl acetate (4×40 ml), the combined extracts were dried over magnesium sulphate and evaporated at 30° C./10 nun Hg, to give 4[5]-diazo-5[4]-dimethylcarbamoylimidazole (1.59 g), in the form of orange crystals, m.p. 101°-103° C. (with decomposition) [Elemental analysis:- found: C,42.6; H,4.17; N,41.4%; $C_6H_7N_5O$ requires: C,43.6; H,4.27; N,42.4%].

The present invention includes within its scope pharmaceutical compositions which comprise, as active ingredient, at least one tetrazine derivative of general formula I, together with a pharmaceutical carrier or coating. In clinical practice the compounds of general formula I will normally be administered orally, rectally, vaginally or parenterally, e.g. intravenously or intraperitoneally.

Methods of presentation of pharmaceutically active compounds are well known in the art and a suitable vehicle may be determined by the physician or pharmacist, depending upon such factors as the effect sought, the size, age, sex and condition of the patient and on the properties of the active compound. The compositions may also contain, as is usual in the art, such materials as solid or liquid diluents, wetting agents, preservatives, flavouring and colouring agents and the like.

Solid compositions for oral administration include compressed tablets, pills, dispersible powders, and granules. In such solid compositions one or more of the active compounds is, or are, admixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert-diluents commonly used in the arts such as water and liquid paraffin. Besides inert diluents such compositions may also comprise adjuvants, such as wetting and suspending agents, e.g. polyvinylpyrrolidone, and sweetening, flavouring, perfuming and preserving agents. The compositions according to the invention, for oral administration, also include capsules of absorbable material such as gelatin containing one or more of the active substances with or without the addition of diluents or excipients.

Solid compositions for vaginal administration include pessaries formulated in manner known per se and containing one or more of the active compounds.

Solid compositions for rectal administration include suppositories fomulated in manner known per se and containing one or more of the active compounds.

Preparations according to the invention for parenteral administration include sterile aqueous or non-aqueous solutions, suspensions, or emulsions. Examples of non-aqueous solvents or suspending media are polyethylene glycol, dimethyl sulphoxide, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions, or by irradiation. They may slo be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. obviously several unit dosage forms may be administered at about the same time. In general, the preparations should normally contain at least 0.025% by weight of active substance when required for administration by injection; for oral administration the preparation will normally contain at least 0. 1% by weight of active substance. The dose employed depends upon the desired therapeutic effect, the route of administration and the duration of the treatment.

The tetrazine derivatives of general formula I are useful in the treatment of malignant neoplasms, for example carcionomas, melanomas, sarcomas, lymphomas and leukaemias, and in the treatment of glioma and mycosis fungoides at doses which are generally between 0.1 and 200, preferably between 1 and 20, mg/kg body weight per day.

The following Composition Examples illustrate pharmaceutical compositions according to the present invention.

COMPOSITION EXAMPLE 1

A solution suitable for parenteral administration was prepared from the following ingredients:

| | |
|---|---|
| 8-Carbamoyl-3-(2-chloroethyl)-[3H]-imidazo[5,1-d]-1,2,3,5-tetrazin-4-one | 1.0 g |
| Dimethyl sulphoxide | 10 ml |
| Arachis oil | 90 ml | by dissolving the 8-carbamoyl-3-(2-chloroethyl)-[3H]imidazo[5,1-d]-1,2,3,5-tetrazin-4-one in the dimethyl sulphoxide and adding the arachis oil. The resulting solution was divided, under aseptic conditions, into ampoules at an amount of 10 ml per ampoule. The ampoules were sealed, to give 10 ampoules each containing 100 mg of 8-carbamoyl-3-(2-chloroethyl)-[3H]-imidazo[5,1-d]-1,2,3,5-tetrazin-4-one.

Similar ampoules containing solutions suitable for parenteral administration may be prepared by proceeding in a similar manner but replacing the 8-carbamoyl-3-(2-chloroethyl)-[3H]-imidazo-[5,1-d]-1,2,3,5-tetrazin-4-one by another compound of general formula I.

COMPOSITION EXAMPLE 2

Capsules suitable for oral administration were prepared by placing 8-carbamoyl-3-(2-chloroethyl)-[3H]imidazo[5,1-d]-1,2,3,5-tetrazin-4-one into gelatin shells of number 2 size at a rate of 10 mg per capsule.

Similar capsules may be prepared by using another compound of general formula I or any other conveniently sized capsule shells.

We claim

1. A [3H]-imidazo[5,1-d]-1,2,3,5-tetrazin-4-one derivative of the formula:

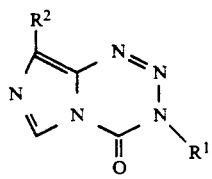

wherein $R^1$ represents hydrogen, or an alkyl, alkenyl or alkynyl group containing from 1 to 6 carbon atoms, or a said group substituted by from one to three substituents selected from halogen atoms, alkoxy, alkylthio, alkylsulphinyl and alkylsulphonyl groups containing up to 4 carbon atoms, and phenyl substituted by alkoxy and alkyl groups containing from 1 to 4 carbon atoms or a nitro group; or $R^1$ represents a cycloalkyl group containing from 3 to 8 carbon atoms, and $R^2$ represents a carbamoyl group, or a carbamoyl group carrying on the nitrogen atom one or two groups selected from alkyl and alkenyl groups containing up to 4 carbon atoms, and cycloalkyl groups containing from 3 to 8 carbon atoms, and—when $R^1$ represents hydrogen—alkali metal salts thereof.

2. A tetrazine derivative according to claim 1 wherein $R^1$ represents an alkyl, alkenyl or alkynyl group substituted by one, two or three optionally substituted phenyl groups and the optional substituents on the phenyl radical(s) are selected from alkoxy and alkyl groups containing up to 4 carbon atoms, and the nitro group.

3. A tetrazine derivative according to claim 1 wherein $R^1$ represents an alkyl group containing from 1 to 6 carbon atoms optionally substituted by one or two halogen atoms or by an alkoxy group containing 1 to 4 carbon atoms or by a phenyl group optionally substituted by one or two alkoxy groups containing from 1 to 4 carbon atoms, or $R^1$ represents an alkenyl group containing 2 to 6 carbon atoms or a cyclohexyl group.

4. A tetrazine derivative according to claim 3 wherein the halogen atom(s) is (or are) chlorine, fluorine and/or bromine, the alkoxy group(s) is (or are) methoxy, and the alkenyl group is allyl.

5. A tetrazine derivative according to claim 1 wherein $R^1$ represents an alkyl group containing from 1 to 6 carbon atoms unsubstituted or substituted by a halogen atom.

6. A tetrazine derivative according to claim 5 wherein $R^1$ represents an alkyl group containing 1 to 3 carbon atoms unsubstituted or substituted by a halogen atom.

7. A tetrazine derivative according to claim 1 wherein $R^1$ represents methyl or a 2-haloalkyl group.

8. A tetrazine derivative according to claim 5 in which the halogen atom on the alkyl group is chlorine or fluorine.

9. A tetrazine derivative according to claim 1 wherein $R^1$ represents 2-fluoroethyl or 2-chloroethyl.

10. A tetrazine derivative according to claim 1 wherein $R^1$ represents a benzyl or p-methoxybenzyl group.

11. A tetrazine derivative according to claim 1 wherein $R^2$ represents a carbamoyl group, a monoalkylcarbamoyl group containing up to 4 carbon atoms in the alkyl radical, or a monoalkenylcarbamoyl group containing up to 4 carbon atoms in the alkenyl radical.

12. A tetrazine derivative according to claim 1 wherein $R^1$ represents an alkyl, alkenyl or alkynyl group containing from 1 to 6 carbon atoms, each such group being unsubstituted or substituted by from one to three halogen atoms, and $R^2$ represents the carbamoyl group.

13. A tetrazine derivative according to claim 1 which is 8-carbamoyl-3-methyl-[3H]-imidazo[5,1-d]-1,2,3,5-tetrazin-4-one.

14. A tetrazine derivative according to claim 1 which is 8-carbamoyl-3-n-propyl-[3H]-imidazo[5,1-d]-1,2,3,5-tetrazin-4-one.

15. A tetrazine derivative according to claim 1 which is 8-carbamoyl-3-(2-chloroethyl)-[3H]-imidazo-[5,1-d]-1,2,3,5-tetrazin-4-one.

16. A tetrazine derivative according to claim 1 which is 3-(2-chloroethyl)-8-methylcarbamoyl-[3H]imidazo[5,1-d]-1,2,3,5-tetrazin-4-one.

17. A tetrazine derivative according to claim 1 which is 8-carbamoyl-3-(3-chloropropyl)-[3H]-imidazo[5,1-d]-1,2,3,5-tetrazin-4-one.

18. A tetrazine derivative according to claim 1 which is 8-carbamoyl-3-(2,3-dichloropropyl)-[3H]-imidazo[5,1-d]-1,2,3,5-tetrazin-4 -one.

19. A tetrazine derivative according to claim 1 which is 3-allyl-8-carbamoyl-[3H]-imidazo[5,1-d]-1,2,3,5-tetrazin-4-one.

20. A tetrazine derivative according to claim 1 which is 3-(2-chloroethyl)-8-dimethylcarbamoyl[3H]-imidazo[5,1-d]-1,2,3,5-tetrazin-4-one.

21. A tetrazine derivative according to claim 1 which is 3-(2-bromoethyl)-8-carbamoyl-[3H]-imidazo[5,1-d]-1,2,3,5-tetrazin-4-one.

22. A tetrazine derivative according to claim 1 which is 3-benzyl-8-carbamoyl-[3H]-imidazo[5,1-d]-1,2,3,5-tetrazin-4-one.

23. A tetrazine derivative according to claim 1 which is 8-carbamoyl-3-(2-methoxyethyl)-[3H]imidazo[5,1-d]-1,2,3,5-tetrazin-4-one.

24. A tetrazine derivative according to claim 1 which is 8-carbamoyl-3-cyclohexyl-[3H]imidazo[5,1-d]-1,2,3,5-tetrazin-4-one.

25. A tetrazine derivative according to claim 1 which is 8-carbamoyl-3-(p-methoxybenzyl)-[3H]imidazo[5,1-d]-1,2,3,5-tetrazin-4-one.

26. A tetrazine derivative according to claim 1 which is 8-(N-allylcarbamoyl)-3-(2-chloroethyl)[3H]-imidazo[5,1-d]-1,2,3,5-tetrazin-4-one.

27. A pharmaceutical composition which comprises a tetrazine derivative as claimed in claim 1 in association with a pharmaceutical carrier.

28. A method for the treatment of a patient with a malignant neoplasm such as a carcinoma, melanoma, sarcoma, lymphoma or leukaemial which comprises administering to the patient a tetrazine derivative as claimed in claim 1 in an amount sufficient to improve for the better the condition of the patient.

29. A method for the treatment of a patient with or requiring an organ or skin graft or suffering from an immunological disease which comprises administering to the patient a suitable amount of a tetrazine derivative as claimed in claim 1.

30. A method for the treatment of a patient with a malignant neoplasm, which comprises administering to the patient a tetrazine derivative as claimed in claim 1 in an amount sufficient to improve for the better the condition of the patient.

31. A method for the treatment of a patient with leukaemia, which comprises administering to the patient a tetrazine derivative as claimed in claim 1 in an amount sufficient to improve for the better the condition of the patient.

32. A method of treating glioma comprising administering to a patient in need of such treatment an effective amount to improve for the better the condition of the patient of a tetrazine derivative as claimed in claim 1.

33. A method of treating mycosis fungoides comprising administering to a patient in need of such treatment an effective amount to improve for the better the condition of the patient of a tetrazine derivative as claimed in claim 1.

* * * * *